United States Patent [19]

Hayamizu

[11] 4,153,834
[45] May 8, 1979

[54] PATTERN PROJECTOR FOR AUTOMATIC FOCUSING ENDOSCOPE

[75] Inventor: Yoshisada Hayamizu, Hachiouji, Japan

[73] Assignee: Olympus Optical Co., Ltd., Tokyo, Japan

[21] Appl. No.: 817,852

[22] Filed: Jul. 21, 1977

[30] Foreign Application Priority Data

Jul. 20, 1976 [JP] Japan .................................. 51-86260

[51] Int. Cl.² .............................................. G01J 1/20
[52] U.S. Cl. .................................... 250/201; 250/227
[58] Field of Search ..................... 350/96.26; 250/227, 250/201, 204, 216

[56] References Cited

U.S. PATENT DOCUMENTS

| 3,561,432 | 2/1971 | Yamaki et al. | 350/96.26 |
| 4,009,386 | 2/1977 | Deml et al. | 250/201 |
| 4,070,116 | 1/1978 | Frosch et al. | 250/201 |

Primary Examiner—David C. Nelms
Attorney, Agent, or Firm—Cushman, Darby & Cushman

[57] ABSTRACT

A pattern projecting system for automatic focusing endoscopes arranged so that light from a pattern of pre-determined shape is imaged on the end face on the observer side of an image fiber arranged in an endoscope, is reflected by the object after passing through the image fiber and objective, inversely transmitted by the image fiber and is detected by a detector after going out from the end face on the observer side of the image fiber. An automatic focusing means is arranged to automatically move the objective along its optical axis, based on the output of the detector.

6 Claims, 4 Drawing Figures

PATTERN PROJECTOR FOR AUTOMATIC FOCUSING ENDOSCOPE

BACKGROUND OF THE INVENTION (a) Field of the invention:

The present invention relates to a pattern projecting system for automatic focusing endoscopes.

(b) Description of the prior art:

When using an endoscope, the operator has to perform various operations such as bending operation for changing the direction of distal end upward, downward, rightward and leftward, operation for injecting water, air, etc. into a body cavity and for sucking them out of the body cavity, operation for cutting off or taking out a sample by means of forceps etc., photographing operation, focusing operation of photographing lens, and so forth. As the operator has to perform many kinds of operations as described in the above, he has to carry out very complicated operations. Therefore, for the operator, it is desirable to omit even one of those operations and omission of focusing operation is also desirable for simplifying the operations. To omit the focusing operation, however, it is necessary to arrange the objective as a fixed focus lens system and to make its depth of focus deep by stopping down the aperture stop. When, however, the aperture stop is stopped down as above, the aperture ratio of the photographing optical system becomes small and it is necessary to make the exposure time long when photographing. However, a long exposure time when photographing an object in a body cavity becomes a cause of blur as the body cavity will move and it will become impossible to obtain a clear photograph.

To solve the above problem so that a clear photograph is obtained by a photographing optical system of large aperture ratio and to simplify the operation of the endoscope, it is necessary to automatically focus the objective. However, automatic focusing in endoscopes has the following problems. The first problem is that the object to be observed or photographed by an endoscope exists in a body cavity and, therefore, the contrast of the object is very low and the difference between the brightness and darkness of the object is very small. So, it is impossible to attain high-accuracy focus detection by a detector when the focus is detected only by the brightness of the object. The second problem is that the diameter of an endoscope is limited and cannot be made large. Therefore, it is impossible to additionally arrange an optical system for focus detection in the distal end of endoscopes. The third problem is as follows. That is, it may be considered to illuminate the object obliquely by utilizing a part of illuminating light and to use it for focus detection. In that case, however, the illuminating light for focus detection does not coincide with the optical axis of the objective, because of change in the distance to the object, when it is attempted to focus the objective by moving it. Therefore, it is not always possible to focus on the center of the field.

SUMMARY OF THE INVENTION

It is, therefore, a primary object of the present invention to provide a pattern projecting system for automatic focusing endoscopes arranged so that light passed through a pre-determined pattern is imaged on the end face on the observer side of an image fiber constituting an endoscope, transmitted by the image fiber, imaged on the object surface, reflected by the object surface and returned, an automatic focusing means for endoscopes being arranged to detect the intensity of returned light and to automatically move a photographing lens, which is arranged on the object side of the image fiber, along its optical axis based on the detected intensity of returned light in order to automatically focus for photographing lens.

Another object of the present invention is to provide a pattern projecting system for automatic focusing endoscopes, arranged so that the light used for automatic focusing enters in end face of the image fiber in the oblique direction in respect to the end face and thereby it is arranged that the light used for automatic focusing does not cause any influence on observation or photographing.

DETAILED DESCRIPTION OF THE PREFERRED EMBODIMENTS

Content of the present invention is described below based on respective embodiments shown on the accompanying drawings.

Figure 1:
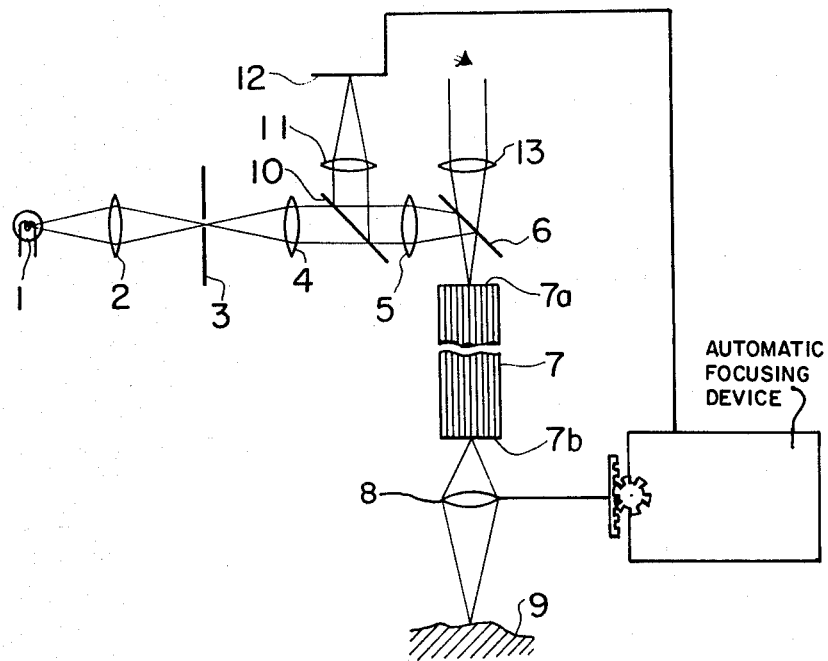
FIG. 1 shows the optical system of Embodiment 1 of the apparatus according to the present invention.

In FIG. 1 showing the optical system of Embodiment 1 of the pattern projecting system according to the present invention, numeral 1 designates a light-source lamp and numeral 2 designates a condenser lens. Numeral 3 designates a pattern of pre-determined shape. In FIG. 1, the pattern 3 has a pinhole. Numeral 4 designates a collimator lens, numeral 5 designates an imaging lens, numeral 6 designates a half mirror, numeral 7 designates an image fiber, numeral 8 designates a photographing lens, numeral 9 designates an object, numeral 10 designates a half mirror, numeral 11 designates an imaging lens, numeral 12 designates a detector, and numeral 13 designates an eyepiece. In the above-mentioned optical system, the light coming from the light-source lamp 1 and passed through the pinhole 3 is imaged at the center of the end face 7a on the observer side of the image fiber 7 by means of the imaging lens 5. The imaged light goes out from the center of the end face 7b on the other end, i.e., on the object side of the image fiber 7, in the same state as it entered the end face 7a and reaches the object 9 through the photographing lens 8. Then, the light is reflected by the object 9 and is returned to the half mirror 10. Then, the light is reflected by the half mirror 10 and is imaged on the detector 12 by the imaging lens 11. When the photographing lens 8 is properly focused in that case, the light emanating from the end face 7b of the image fiber 7 forms an image of the pinhole 3 on the object surface and the intensity of light reflected by the object surface and detected by the detector 12 becomes the highest. Therefore, it is possible to perform automatic focusing by moving the photographing lens based on the intensity of light detected by the detector 12 so that the intensity of light becomes the highest.

If, in this pattern projecting system, the light from the pinhole reflected by the object and used for automatic focusing enters the observing or photographing optical system passing through the half mirror 6, the light will disturb observation or, at the time of photographing, the image of the pinhole will be photographed together with the image of the object. This will be prevented by closing the pinhole or extinguishing the illuminating lamp just before observation or photographing.

When it is so arranged that the image of the pinhole is formed just before automatic focusing and disappears when automatic focusing is completed, no influence occurs on observation and photographing. For this purpose, it may be arranged for example so that the image of the pinhole is formed by putting on the light source lamp 1 by depressing a push button or the like when it is required to perform automatic focusing and that the light source lamp is put out at the same time as focusing is completed. Alternatively, it may be arranged so that the image of the pinhole is formed, at the time of photographing, by depressing a push button in the same way as above and that the image of the pinhole is extinguished and photographing is carried out in succession by depressing the push button when focusing is completed. To perform automatic focusing operation more easily and accurately, it is preferable to arrange that the intensity of illuminating light for observation is reduced at the time of focusing.

Figure 2:
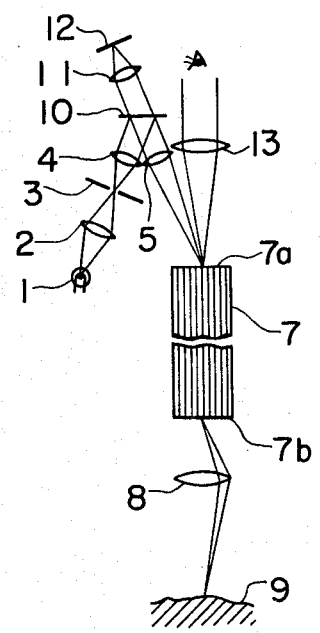
FIg. 2 shows the optical system of Embodiment 2.

The optical system shown in FIG. 2 relates to Embodiment 2 of the present invention. The difference of Embodiment 2 from Embodiment 1 is that the optical system comprising the light source lamp 1, condenser lens 2, pinhole 3, etc. is arranged in the state that its optical axis is inclined so that the light from the imaging lens 5 obliquely enters the end face 7a of the image fiber 7. The other arrangement is substantially the same as Embodiment 1.

When the optical system is arranged as above, the light from the pinhole 3 entered the end face 7a on the observer side of the image fiber 7 goes out from the end face 7b on the object side of the image fiber 7 in the same condition as it entered the end face 7a, i.e., goes out in oblique direction in respect to the end face 7b, as it is evident from FIG. 2, and is imaged on the object surface by means of the objective 8. Therefore, by Embodiment 2, it is also possible to perform automatic focusing in the same way as Embodiment 1 shown in FIG. 1. In case of Embodiment 2, however, the light used for automatic focusing is obliquely incident on the object surface and, therefore, almost no portion of the light for automatic focusing directly enters the observing optical system after it is reflected by the object. Consequently, the light used for automatic focusing does not disturb observation or photographing. Therefore, it is not necessary to close the pinhole or to extinguish the light source lamp when focusing is completed.

Figure 3:
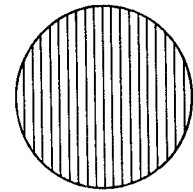
FIg. 3 and 4 respectively show two alternative examples of patterns to be used in the pattern projecting system according to the present invention.
Figure 4:
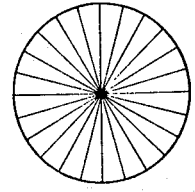

In the embodiments described in the above, the pattern used for automatic focusing is a pinhole. However, a pattern of any other shape may be used instead of the pinhole. As examples of patterns, FIG. 3 shows a pattern of parallel stripes and FIG. 4 shows a pattern of radial stripes.

As explained in the above, by the pattern illuminating system according to the present invention, it is possible to perform automatic focusing by arranging only a simple optical system, which comprises a light source lamp, pattern, imaging lens, etc., on the observer side of the image fiber and, therefore, the diameter of the distal end of the endoscope does not become large. Moreover, it is not necessary to perform focusing of the photographing lens by manual operation. Therefore, the number of operations to be performed by the operator is reduced and, moreover, it is possible to obtain a favourable image of the object.

I claim:
1. An endoscope system, comprising:
   (a) an image fiber having an object end and an observer end;
   (b) a light intensity detector related to the observer end of the image fiber for detecting the intensity of light emanating from the observer end of the image fiber;
   (c) a focusing lens adjustably related to the image fiber so that when the observer end of the image fiber is aimed at an object, the focusing lens may be adjusted to maximize an intensity of illumination at the detector as an indication that the object has been brought into focus upon the detector;
   (d) a pattern having at least two adjoining sharply contrasting regions;
   (e) means for illuminating said pattern;
   (f) an optical system for projecting said pattern, as illuminated by said illuminating means, upon the observer end of said image fiber for transmission through said image fiber and onto said object, whereby:
   even though said object may have no regions of sufficiently high contrast as to otherwise permit detection at the detector of when said object has been brought into focus at the detector, the reflection of the projection of said illuminated pattern from said object as detected at said detector provides said sufficiently high contrast; and
   (g) said detector being so arranged relative to the image fiber observer end that said reflection reaches said detector from said object without intermediately reaching the illuminated pattern.

2. The endoscope system of claim 1, further including:
automatic means operatively connecting said detector with said adjustably related focusing lens, for automatically adjusting said focusing lens in response to detection of illumination at said detector to maximize detection of illumination at said detector.

3. The endoscope system of claim 1, wherein:
said image fiber observer end has an end face; and
said optical system is arranged to have the optical axis thereof obliquely inclined in respect to an imaginary line perpendicular to said end face.

4. The endoscope system of claim 1, wherein:
one of said sharply contrasting regions of said pattern is constituted by a pin hole.

5. The endoscope system of claim 1, wherein:
said pattern is constituted by a plurality of contrasting parallel stripes.

6. The endoscope system of claim 1, wherein:
said pattern is constituted by a plurality of contrasting, radiating stripes.

* * * * *